United States Patent [19]
Palumbo

[11] Patent Number: 5,294,536
[45] Date of Patent: Mar. 15, 1994

[54] CONJUGATES

[75] Inventor: Paul S. Palumbo, West Newton, Mass.

[73] Assignee: PB Diagnostic Systems, Inc., Westwood, Mass.

[21] Appl. No.: 872,539

[22] Filed: Apr. 23, 1992

[51] Int. Cl.$^5$ ............ G01N 33/543; C12N 9/96; C07K 17/06
[52] U.S. Cl. ............ 435/7.93; 435/188; 436/527; 436/529; 436/532; 530/391.1; 530/391.9; 530/395; 530/405
[58] Field of Search ............ 548/546; 435/188, 7.93; 530/391.9, 395, 391.1, 405; 436/529, 527, 532

[56] References Cited

U.S. PATENT DOCUMENTS

| | | | |
|---|---|---|---|
| 4,150,033 | 4/1979 | Kitagawa | 260/326.26 |
| 4,214,048 | 7/1980 | Kitagawa | 435/7 |
| 4,760,142 | 7/1988 | Primes et al. | 544/287 |
| 4,994,385 | 2/1991 | Bieniarz et al. | 435/188 |
| 5,002,883 | 3/1991 | Bieniarz et al. | 435/176 |

FOREIGN PATENT DOCUMENTS

| | | |
|---|---|---|
| 314042 | 5/1989 | European Pat. Off. |
| 0314127 | 5/1989 | European Pat. Off. |
| 0396116 | 11/1990 | European Pat. Off. |

OTHER PUBLICATIONS

"Chemical Modifications of Proteins: History and Applications"—G. E. Means & Robert E. Feeney, Bioconjugate Chem., 1, pp. 2–12, 1990.

"A Brief Survey of Methods For Preparing Conjugates with Dyes Haptens, and Cross-Linking Reagents"—M. Brinkley, Bioconjugate Chem., 3, pp. 2–13, 1992.

"Recent Advances with Monoclonal Antibody Drug Targeting For The Treatment of Human Cancer"—G. A. Koppel, Bioconjugate Chem., 1, pp. 13–23, 1990.

"Preparation and Characterization of Hetero-Bifunctional Cross-Linking Reagents For Protein Modification"—Kitagawa, T., et al., Chem. Pharm. Bull., vol. 29, (4), pp. 1130–1135.

"Attachment of Rhodosaminylanthracyclinone-Type Anthracyclines to the Hinge Region of Monoclonal Antibodies"—Hermentin, P., et al., Bioconjugate Chem., 1, pp. 100–107, 1990.

"Kinetics of Base-Catalyzed Hydrolysis of Urea'"—Lynn, K. R., J. Phys. Chem., vol. 69, No. 2, pp. 687–689, 1965.

"Esters and Carbamic Acid"—P. Adams et al., Chem. Rev., pp. 567–602, 1965.

B. Rao, J. Polym. Sci., Part A: Polym. Chem., vol. 27(8), pp. 2509–2518 (1989).

*Primary Examiner*—Mary E. Ceperley
*Attorney, Agent, or Firm*—Gaetano D. Maccarone

[57] ABSTRACT

A compound represented by the formula

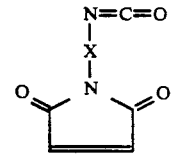

wherein X is a spacer group. The compound is useful for conjugating a compound having an alcohol group or an amine group to a compound having a thiol group. The compound can be used to conjugate a biologically active group such as an antigen to a protein such as an enzyme to provide an enzyme-labeled antigen for use in enzyme-amplified immunoassay methods for analytes or metabolites in sample fluids. The compound can also be used to immobilize a material such as a protein to a solid support.

14 Claims, 1 Drawing Sheet

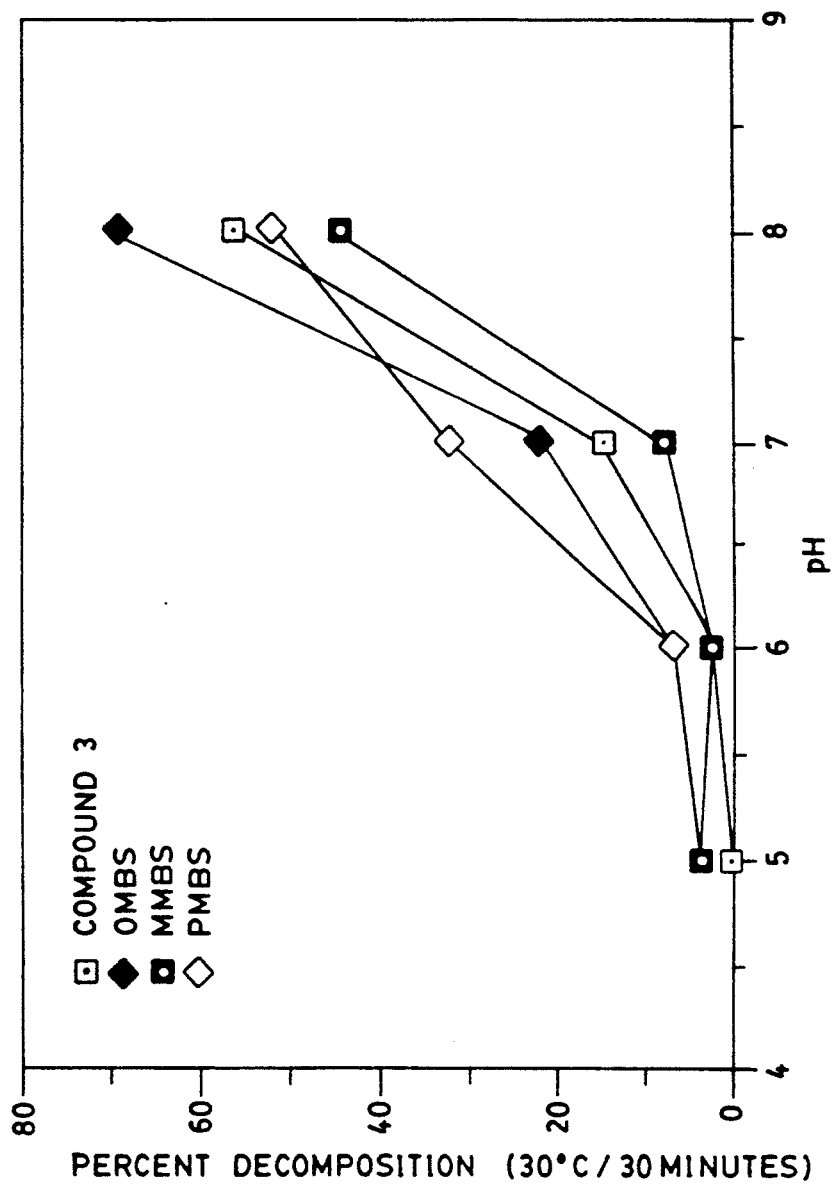

CONJUGATES

BACKGROUND OF THE INVENTION

The application is directed to novel maleiimido compounds and conjugates made therefrom.

Progress in immunochemistry has required the preparation of numerous protein-protein or protein-hapten conjugates for analytical and preparative techniques. For a review of protein modifications see Means, G. E. and Feeney, R. E., *Bioconjugate Chem.*, (1990), 1, 2–12 and M. Brinkley, *Bioconjugate Chem.*, (1992) 3, 2–13. The attachment of cytotoxic drugs to tumor-localizing monoclonal antibodies (immunotoxins) is an approach to chemotherapy which is rapidly gaining acceptance. See Koppel, G. A., Bioconjugate Chem., 1990, 1, 13–23. Many reagents for the preparation of such conjugates have been disclosed and studied extensively. See Kitagawa et al, Chem. Pharm. Bull., 29(4), 1130–1135 (1981) and references cited therein. The so-called cross-linking reagents which have been developed are typically designed to have specific reactivity with functional groups contained in each reactant. Both homoand heterobifunctional reagents are known with the latter being most desirable. Since heterobifunctional cross-linkers possess two selectively reactive groups which can be used to link proteins or other moieties in a stepwise and specific manner, the occurrence of unwanted side reactions such as the formation of homo-protein polymers is desirably avoided.

A common type of heterobifunctional crosslinker contains an amine reactive group (e.g., N-hydroxysuccinimide esters) and a sulfhydryl reactive group (e.g., maleiimide, haloacetyl functions and reactive disulfides) connected by a spacer group. However, there are instances where a hapten and/or a peptide does not contain one of the common functional groups such as an ε-amino-lysine residue and linking such materials to proteins becomes increasingly more difficult. Conventional crosslinkers are inadequate for this purpose. One approach is to chemically modify the material, but this technique is not satisfactory in all instances since this often changes the desired biological or chemical behavior of the compound. While the compound of interest may lack a linkable amino group it may contain a hydroxyl group. Known crosslinking materials may be used with such compounds but the resulting ester-linked derivatives typically suffer from the stability limitations inherent in the ester moiety. See, for example, Hermentin, P. et al. *Bioconjugate Chem.*, 1990, 1, 100–107. Crosslinking chemistry which typically provides more stable hydroxyl linking such as in the formation of a urethane bond from an isocyanate and an alcohol group is always preferred. See, for example, Lynn, K. R. et al, *J. Phys. Chem.*, 1972, 69, No. 2, pp. 687–689 and Adams, P. et al., *Chem. Rev.*, 1965, 65, 567.

Accordingly as the state of the art advances there is a continuing demand for new materials to perform these functions.

It is therefore the object of this invention to provide novel heterobifunctional compounds.

It is another object to provide heterobifunctional compounds which can link a compound having an alcohol group or an amine group with a compound having a thiol group.

A further object is to provide heterobifunctional compounds which have a terminal isocyanate group and a terminal maleiimido group.

SUMMARY OF THE INVENTION

These and other objects and advantages are accomplished in accordance with the invention by providing novel compounds which include both an isocyanate group and a maleiimido group. These compounds are represented by the formula

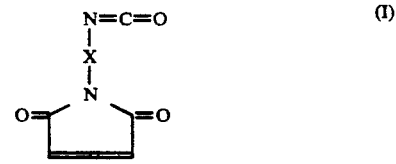

wherein X is a spacer group. The isocyanate group is a highly reactive, sterically unencumbered functionality which will react with amines to form ureas and with alcohols to form urethanes (carbamates). The maleiimido group is reactive with thiol (sulfhydryl, R—SH), groups. Thus, these compounds can be used to link compounds which contain a thiol group, for example, an enzyme, with compounds which contain an alcohol group and/or an amine group.

The spacer group, X, serves several functions. One important function of the spacer group is its effect on steric hindrances. Linear bridging between protein and/or hapten moieties with minimal steric interaction can be a requirement for maintaining desired immunoreactivity. The spacer group, X, can be alkylene, preferably having from 1 to 6 carbon atoms, a saturated carbocyclic moiety such as cyclohexyl or an aromatic carbocyclic moiety such as phenyl or naphthyl. The saturated and aromatic carbocyclic moieties may be substituted with one or two alkyl groups having from 1 to 6 carbon atoms through which the attachment to the isocyanate and/or the maleiimide moieties is made. Where X is a saturated carbocyclic moiety it is preferred to include one methyl substituent and to attach the maleiimide group through the methyl substituent.

It should be noted here that the rings of the saturated and aromatic carbocyclic moieties can be further substituted with substituents such as dimethylamino, methoxy, ethoxy, methyl, ethyl, sulfonamido, sulfonic acid, etc.

The conjugates provided according to the invention are represented by the formula

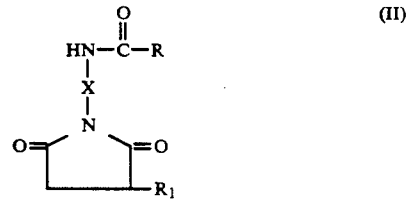

wherein R is the residue of a compound containing an alcohol group and/or an amine group; $R_1$ is the residue of a compound containing a sulfhydryl group; and X is as previously defined. It will be apparent to those skilled in the art that the moiety represented by R is linked to the carbonyl group through an oxygen or nitrogen atom and the moiety represented by $R_1$ is linked to the maleiimide moiety through a sulfur atom.

Generally, the R moiety can be the residue of antigens (including haptens), synthetic or recombinant peptide sequences, steroids and the like. $R_1$ can be the residue of any thiol group-containing compound such as antibodies, enzymes and the like. In preferred embodiments, as will be described in detail, there are provided enzyme-labeled moieties such as enzyme-labeled antigens (including haptens), enzyme-labeled peptides or polypeptides, etc. for use in immunoassay techniques and antibodies linked to solid support materials.

BRIEF DESCRIPTION OF THE DRAWING

The FIGURE is a graphical illustration comparing the relative stability of a maleiimide derivative of a heterobifunctional intermediate according to the invention, as a function of pH, to several known compounds.

DESCRIPTION OF THE PREFERRED EMBODIMENTS

The preparation of the novel heterobifunctional compounds of the invention will be apparent to those skilled in the art from their general knowledge of synthetic preparative techniques together with the general disclosure and specific examples provided herein. Generally, the preparation of these heterobifunctional crosslinking compounds involves a Curtius rearrangement of the corresponding acyl azide. The starting maleiimido acid compounds can be prepared according to procedures described in the literature. For the preparation of aromatic maleiimide carboxylic acids see: Yoshitake et al, Eur. J. Biochem., 101 (1979), 395–399; for the preparation of aliphatic maleiimide carboxylic acids see: Keller et al, J. Helv. Chem. Acta, 58 (1975) 531. The maleiimido carboxylic acid compounds prepared in this manner are treated with one equivalent of triethylamine (TEA) followed by one equivalent of diphenyl phosphoryl azide (DPPA) in toluene. Heating at reflux initiates the rearrangement of the implied acylazide and affords the isocyanate according to the following equation:

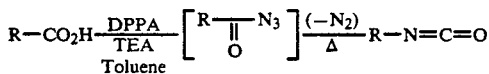

Other methods for converting an acid to an isocyanate group are known in the literature. See Banthrope, in Patai, "The Chemistry of the Azido Group", pp 397–405, Interscience Pub., New York 1971; Smith, Org. React. 3 pp 337–449 (1976).

As noted previously the conjugates (Formula II) according to the invention include a wide variety of materials. The -R moiety is the residue of a compound containing an alcohol and/or an amino group. While it is preferred to utilize compounds which include naturally present alcohol or amine groups, the compounds may be derivatized to include one or more of such groups. Techniques for introducing alcohol and amine groups in compounds are well known in the art. See "Advanced Organic Chemistry", 2nd ed., J. March (1977), McGraw Hill, Inc., New York.

Any compound which includes an alcohol or amine group which will react with the isocyanate group in the heterobifunctional compounds of the invention to form a stable covalent bond may be incorporated in the conjugates. Such compounds include:

Natural, recombinant or synthetic peptides or polypeptides containing serine groups such as synthetic peptides derived from the transmembrane glycoprotein (GP 41) of the HIV-1 virus or peptides derived from the glycoprotein 42 of the HIV-2 virus;

A variety of natural or synthetic biologically active substances such as folic acid, vitamin $B_{12}$, digoxin, digitalis glycosides, antibiotics such as vancomycin, aminoglycosides such as amikacin, methotrexate, carbamazepine, etc., and therapeutic drugs such as theophylline, phenytoin, phenobarbital, etc.;

Hormones such as 3,5,5'-triiodothyronine (T3), 3,5,3',5'-tetraiodothyronine (T4), cortisol, estradiol and the like; and Steroids such as cholesterol.

The thiol group-containing compound can be any which will react with the maleiimide group in the heterobifunctional compounds of the invention to form a stable covalent bond. Such compounds include:

Enzymes such as β-D-galactosidase which contain a thiol group or those such as peroxidase, glucose oxidase and alkaline phosphatase into which a thiol group can be introduced. The introduction of thiol groups in enzymes can be carried out as described in Archives of Biochemistry and Biophysics, Vol. 96, pp 605–612 (1962);

Compounds such as antibodies, including F(ab')$_2$ fragments, which contain disulfide bonds which can be reduced to thiol groups by known techniques. See, for example, Cleland, W. W., Biochemistry, 1964, 3, 480–482. This group of compounds also includes proteins such as all immunoglobulins, polypeptides such as insulin or human chorionic gonadoptropin (HCG) as well as synthetic peptides which contain an internal disulfide bond.

In addition there are well known techniques for introducing thiol groups in any biologically active substance. See, for example, Blättler, W. A., et al., Biochemistry, 1985, 24, 1517–1524.

Dimethylsulfoxide (DMSO) has been found to be a preferred solvent for the isocyanate reaction in light of its catalytic effect. Generally, the alcohol-and/or amine group-containing compound is combined with one equivalent of the heterobifunctional compound is DMSO and stirred at room temperature under dry nitrogen until conversion of the product is confirmed by thin layer chromatography analysis. In cases where surreptitious water may be present or is present in the form of hydrated reactants, excess reagent can be added to first consume the residual water and then complete the conversion to the desired product. The final products are generally purified by flash chromatography on either reversed or normal phase silica. The use of solvents which may react with the maleiimide moiety, i.e., ammonium hydroxide or other amine-containing solvents, should be avoided. Studies carried out with a model compound, as will be described in detail in an example, indicate that the stability of the resulting maleiimide moiety decreases at pH>7. Maleiimides, however, react specifically with free sulfhydryl groups in a facile way under slightly acidic to neutral conditions (pH 6.5–7.5). The derivatized materials can be dissolved in the appropriate buffers just prior to use with no significant decomposition experienced. Where water solubility is a factor the derivatized compounds can be introduced in a small amount of solvent such as dimethylformamide.

In a preferred embodiment of the invention there are provided conjugates of enzymes linked to antigens. Such conjugates are useful in the well known enzyme-linked immunoassay methods (ELISA) for the determination of analytes or metabolites in fluids such as blood, plasma or serum. These methods include both competitive and sandwich ELISA techniques. These immunoassay techniques are described in U.S. Pat. Nos. 3,654,090 and 3,850,752. The ratio of the enzyme to the antigen or antibody in such conjugates can vary dependent upon the particular enzyme, antigen and antibody, particularly on the number of alcohol or amine groups in the one reactant and the number of thiol groups in the other. Preferably, such enzyme-linked antibody or antigen conjugates include about 3 to 7 molecules of antigen or antibody per molecule of enzyme.

In another preferred embodiment there are provided conjugates of proteins such as antibodies or enzymes bound to solid support materials which include an alcohol or amine group. Such solid supports include any which can be reacted with the isocyanate group of the heterobifunctional compounds to form a stable covalent bond. Alternatively, the proteins may be attached through the isocyanate group and the resulting intermediate reacted with a thiolated solid support material. The solid phase materials can be in the form of large molecules such as dextran, sugars and the like, microparticles, beads, sheets, spheres, fibrous materials, such as chemically modified glass fibers, filters, etc. The materials may be polystyrene aminated particles, amino silica gels, partially hydrolyzed nylon, partially reduced polyarylamides, partially reduced cyanoacrylates and the like.

In another preferred embodiment the heterobifunctional compounds of the invention can be utilized to prepare biotinylated conjugates. This can be accomplished by initially reacting a compound, e.g., vitamin $B_{12}$, with PMBI in accordance with the invention and subsequently reacting the product with aminoethanethiol to provide a conjugate with terminal amine groups. The conjugate can then be reacted with commercially available biotin—NHS derivatives to give biotinylated derivatives.

EXAMPLES

The invention will now be further described with respect to specific preferred embodiments by way of examples, it being understood that these are intended to be illustrative only and the invention is not limited to the materials, processes, etc. recited therein.

EXAMPLE I

Preparation of p-maleiimidobenzene isocyanate (PMBI)

4-aminobenzoic acid (4.26 g/31 mmol) was suspended in 30 ml of acetone and solubilized by the addition of 5 ml methanol. A solution of maleic anhydride (3.66 g/37 mmol) in 10 ml acetone was added dropwise and the resulting precipitate stirred for 20 minutes and then suction filtered, washed with acetone and vacuum dried to afford 6.36 gms of a yellow powder. The powder was dissolved in acetic anhydride (13 ml), treated with sodium acetate (1.08 g) and then heated with stirring to 50° C. for 2 hours. The volatile matter was removed under vacuum and the residue taken up in 150 ml of water and heated at 70° C. for 2.5 hours. The resulting white precipitate was suction filtered, washed with water and dried under vacuum overnight to give 4.7 g (70% yield) of 4-maleiimidobenzoic acid. Analysis by silica TLC (10% methanol in methylene chloride) visualized by UV absorption and iodine vapor staining showed one spot at Rf 0.8. The structure was confirmed by NMR spectroscopy.

A stirred suspension of the previous product (4.3 g/20 mmol) in 150 ml of toluene was treated with triethylamine (3.04 ml/22 mmol) and then with diphenylphosphoryl azide (4.7 ml/22 mmol) immediately thereafter. After stirring at room temperature for 2 days the volatile matter was removed under vacuum and the resulting residue chromatographed on silica gel with methylene chloride as the eluent. The product, 4-maleiimidobenzoyl azide, was eluted as a pale yellow crystalline mass (3.9 gms; 91% yield). A sample recrystallized from methylene chloride showed the following behavior in a melting point apparatus: at 115°-120° C. the sample appeared to "pop"; at 125°-130° C. the sample decomposed with vigorous gas evolution. The structure of the compound was confirmed with NMR and IR spectroscopy.

A solution of the azide (3.4 g/14 mmol) in 150 ml of dry toluene was refluxed under nitrogen for 80 minutes and then evaporated under vacuum. This gave 3 g of p-maleiimidobenzene isocyanate (PMBI) represented by the formula

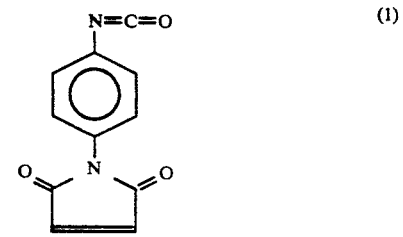

as yellow micro needles. The structure of the product was confirmed by IR and NMR spectroscopy. m.p.=121°-123° C. (CH$_2$Cl$_2$).

A small sample (38 mg) was dissolved in 1 ml methylene chloride and treated with excess methanol (0.15 ml). After 1 hour the volatile material was removed under vacuum to afford methyl N-(p-maleiimidophenyl) carbamate, compound 2. The structure of the product was confirmed by NMR, MS and UV/VIS spectroscopy.

EXAMPLE II

Activation of N-CBZ-Gly-Gly-Ser

A solution of N-CBZ-Gly-Gly-Ser from Sigma Chemical Co. (218 mg/0.62 mmol) in DMSO (4 ml) was treated with PMBI (264 mg/1.23 mmol) and the resultant yellow solution stirred at room temperature for 2¼ hours. The reaction mixture was quenched with 14 ml water (ice bath cooling), stirred for ten minutes at 0°-5° C., suction filtered, washed with excess water and dried under vacuum. The resulting residue was chromatographed on silica with acetic acid-methanol-methylene chloride (1:10:89) to afford the pure product represented by the formula

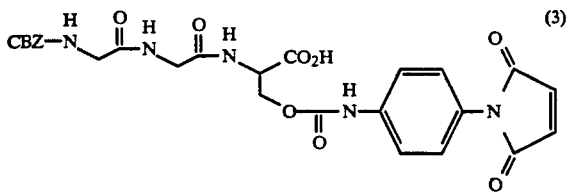

The structure of the compound was confirmed by NMR and MS spectroscopy.

EXAMPLE III

Maleiimide stability study of compound 3

The stability of the maleiimide moiety of the activated peptide prepared in Example II (compound 3) was studied and shown to be comparable to that of three similar compounds, namely the -o-, m- and p-maleimidobenzoic acid —NHS esters (OMBS, MMBS and PMBS, respectively) disclosed by Kitagawa et al., H. Chem. Pharm. Bull., 29 (4), 1130–1135 (1981). In the study a 20 μl aliquot of a 10 mM solution of the activated peptide (2) was incubated in 0.5 ml of 0.05M phosphate buffer (pH 6, 7 or 8) or 0.05M acetate buffer (pH 5) for 30 minutes at 30° C. (in duplicate). Subsequently, 200 μl of 1 mM mercaptoethanol in 0.05M phosphate buffer (pH 6) were added, mixed well for 1–2 minutes and then treated with 1.1 ml of 0.2M Tris-HCl buffer (pH 8.2) containing 0.02M EDTA ·Na$_4$ and then 0.2 ml of methanolic dinitrobenzoic acid were added. After ten minutes the absorbance value at 412 nm of each test sample, i.e., (A) a zero blank; (B) without incubation; and (C) the sample blank [in 20 μl DMF instead of the sample solution, incubated at 30° C. for 30 minutes] was obtained. The percent decomposition of the maleiimide residue was calculated as $[(A-B)/(C-B)] \times 100$. The results are shown in Table 1 and the Figure. The Figure also includes for comparison data for OMBS, MMBS and PMBS (o-, m- and p-maleiimidobenzoic acid. NHS esters, respectively).

| pH | A | B | C | % Decomposition |
| --- | --- | --- | --- | --- |
| 5 | 0.23 | 0.23 | 1.56 | 0.0 |
| 6 | 0.29 | 0.26 | 1.55 | 2.3 |
| 7 | 0.43 | 0.24 | 1.61 | 14.0 |
| 8 | 1.02 | 0.28 | 1.53 | 56.0 |

EXAMPLE IV

A. Activation of vitamin $B_{12}$

A solution of Cyanocobalamin (54 mg/0.04 mmol) in 0.5 ml DMSO was treated with PMBI (97.3 mg./0.45 mmol) and the resultant red solution stirred under argon at room temperature, protected from light, for an overnight period. The mixture was treated with 10 ml ether and stirred vigorously to extract the DMSO. The liquid was decanted from the red oil and again stirred with ether (10 ml). After decanting the liquid, the remaining red oil was triturated with methylene chloride to afford a red powder which was suction filtered, washed with excess methylene chloride and dried under vacuum. The product was purified by flash chromatography on C-18 silica using a methanol-water mixture (2:3) as the eluent. The product eluted as a red band and was isolated upon evaporation of solvent under vacuum to give an activated vitamin $B_{12}$ derivative (41 mg; 66% yield).

The structure of the product was confirmed by NMR, MS and UV/VIS spectroscopy.

B. Linking of the maleiimido-activated vitamin $B_{12}$ to thiolated alkaline phosphatase Alkaline phosphatase (1 mg/7.1 mmol) was thiolated by treatment in 1 ml tris saline magnesium zinc (TSMZ) buffer (pH 7.3) with 2-iminothiolane·HCl in TSE/-NaOH solution (50 μl of solution containing 100 mM each of triethanolamine, sodium chloride, sodium hydroxide and 1 mM of ethylenediamine tetracetic acid) and incubating for twenty minutes at room temperature. After treatment with 10 μl of 1M glycine the excess reagents were removed using a PD-10 column (Sephadex G-25M) eluting with TSMZ buffer (pH 7.3). The fractions containing the derivatized alkaline phosphatase (analysis for free thiol groups using TNBS reagent revealed 4–7 thiol groups per alkaline phosphatase molecule) were pooled (absorbance reading at 280 nm) and then treated immediately with the derivatized vitamin $B_{12}$ (213 n mol). The solution was stored at room temperature for 1 hour and then at 10° C. overnight. Gel filtration in a PD-10 column using TSMZ buffer (pH 7.3) as the eluent separated the alkaline phosphatase-vitamin $B_{12}$ conjugate from the excess derivatized vitamin $B_{12}$ reagent. Spectral analysis of the resulting conjugate relating absorbance at 550, 520, 361 and 280 nm gave a calculated $B_{12}$ protein ratio of about 9:1.

EXAMPLE V

A. Preparation of an amino-substituted vitamin $B_{12}$

To a stirred solution of the maleiimido-activated vitamin $B_{12}$ (3.88 mg/0.00247 mmol) in 0.5 ml of 10% water/90% methanol there was added 0.31 ml of a 1 mg/ml solution of 2-aminoethanethiol hydrochloride (0.00272 mmol) in water. The resultant mixture was stirred at room temperature for 30 minutes. At this point reversed phase TLC revealed the formation of one new product at Rf~0.1 (C-18 silica with 10% water/90% methanol as the eluent).

B. Preparation of an L.C. Biotin-vitamin $B_{12}$ derivative

To this stirred reaction product obtained above there was added 3 mg of NHS-LC-Biotin (from Pierce Chemical Co.) and 0.5 ml pH 8 borate buffer. Stirring was continued overnight followed by purification on reversed phase silica by addition of the crude reaction mixture to a C-18 column which had been equilibrated with 60% water/40% methanol. The column was eluted to remove two pale red bands and the product was removed with 40% water/60% methanol (Rf~0.3 on C-18 TLC with this eluent). Evaporation of the pooled product fraction afforded the purified vitamin $B_{12}$-L.C.-Biotin compound as a red solid (38% yield). The UV/Vis spectrum in water gave three major bands at 361 nm, 516 nm and 549 nm.

EXAMPLE VI

A. Activation of a synthetic peptide derived from the glycoprotein-42 of the HIV-2 virus A thirty five fold molar excess of solid PMBI was added to a solution of 0.5 mg of an HIV 2 specific peptide dissolved in 0.5 ml of DMSO. The mixture was incubated for one hour at room temperature and the reaction was then stopped by adding 0.5 ml of deionized water. The activated peptide was purified by gel filtration chromatography over a 1.5×15 cm. column Bio-Gel P2 equilibrated with 10 mM acetate pH 5.0. The peptide containing fractions were pooled and stored at 4° C.

B. Linking of the activated peptide to thiolated alkaline phosphatase

Thiolated alkaline phosphatase was prepared by incubating 1 mg of the enzyme with one twentieth dilution of 100 mM of 2-iminothiolane .HCl for twenty minutes at room temperature. The activated enzyme was separated from excess reagent by chromatography over a Pharmacia PD-10 column equilibrated with TSMZ pH 7.3 buffer.

The activated enzyme was reacted with a seven fold excess of activated peptide at pH 7.0. The pH of the mixture was adjusted with a 10% solution of triethanolamine. The reaction was quenched after eighteen hours with maleiimide and purified over a 1.5×15 cm column of Sephadex G-75 equilibrated with TSMZ pH 7.3 buffer.

EXAMPLE VII

An assay for HIV antibodies in patient samples of serum was carried out according to the following method using the enzyme conjugated peptide described in Example VI.

An assay module was prepared which included an approximately 1 cm$^2$, 0.42 mm thick porous glass fibrous mesh pad (Whatman GF/F) having immobilized thereon a fusian protein incorporating the binding domains of Protein A and Protein G (Protein A/G available from Pierce Chemical Co.).

A total of 10 μl of sample was added to a solution of 190 μl of the enzyme conjugated peptide of the invention and diluted to the desired concentration in a buffer consisting of 50 mM tris [hydroxymethyl]-aminomethane, (TRIS) Ph 7.6, 150 mM NaCl, 1 mM MgCl$_2$, 0.1 mM ZnCl$_2$, 0.1% Triton×100, 1% gelatin and 1% BSA. The reaction mixture was incubated for six minutes at 37° C.

Subsequently 15 μl of the sample/labeled conjugate mixture was applied to the fibrous pad and the module incubated at 37° C. for six minutes following which 75 μl of a substrate/wash solution consisting of 1 mM of methyl umbelliferyl phosphate and 1M diethanolamine with 0.1% Triton×100 was applied to one end of the fibrous pad through a wash port of the module. The substrate/wash solution was allowed to enter the fibrous pad and propagate through it by capillary action thereby washing the sample area. The module was then incubated at 37° C. for four minutes.

Readings were taken of the reaction zone at regular intervals over a three minute period using a front surface fluorometer by directing 360 nm radiation through an opening in the assay module beneath the reaction zone and collecting the reflected 450 nm radiation. The increase in fluorescence, a function of the amount of enzyme-labeled conjugate bound by the peptide-specific antibody in the sample, was calculated. The result obtained was compared to the results obtained with defined negative and positive calibrators and was determined to be positive or negative on the basis of a determined cutoff value.

The alkaline phosphatase labeled peptide identified correctly all six HIV 2 positive sera and all thirty HIV negative sera which were tested.

EXAMPLE VIII

A. Activation of 11-α-hydroxyprogesterone

A solution of 11 α-hydroxyprogesterone (94 mg/0.28 mmol) in DMSO (2 ml) was treated with PMBI (94 mg/0.43 mmol) and the resultant mixture stirred at room temperature overnight. The product was precipitated by the addition of 10 ml water, with cooling, followed by suction filtration and drying in air overnight. The product was purified by chromatography on silica gel using 2% methanol in methylene chloride as the eluent. The major highest Rf material was isolated to give 90 mg (58% yield) of an 11 α-maleiimide-derivatized progesterone as a pale yellow, crystalline solid.

B. Linking of the maleiimide-activated 11 α-hydroxyprogesterone to thiolated alkaline phosphatase The derivatized progesterone was reacted with the thiolated alkaline phosphatase in accordance with the procedure described in Example IV to provide a progesterone-alkaline phosphatase conjugate.

C. Preparation of a standard curve for a progesterone assay

The progesterone-alkaline phosphatase conjugate was used in a competitive progesterone assay carried out with standard solutions having known progesterone concentrations. The assays were carried out with assay modules of the type described in Example VII. An anti-progesterone monoclonal antibody (35 μl of a 25 mg/ml solution) immobilized on the fibrous solid carrier was employed as the capture material. Initially the standard solution was applied to the fibrous solid carrier followed by a period of incubation. The conjugate solution was then applied to the reaction zone and after a period of incubation the substrate wash solution was applied to an end area of the fibrous solid matrix. A standard curve having a desirably steep slope in the concentration range of interest was obtained.

EXAMPLE IX

A. Activation of β-estradiol

A solution of β-estradiol (35 mg/0.13 mmol) in 1 ml DMSO was treated with PMBI (28 mg/0.13 mmol) in one portion. The resultant yellow solution was stirred overnight at room temperature under argon while protected from light. The crude product was precipitated by addition of excess water and then suction filtered, washed with water and dried under vacuum. The residue was chromatographed on silica with 1% methanol in methylene chloride as the eluent to give 21 mg (33% yield) of a 17 β maleiimide activated β-estradiol product.

B. Linking of the maleiimide activated β-estradiol to thiolated alkaline phosphatase The derivatized estradiol was reacted with alkaline phosphatase in accordance with the reaction scheme described in Example IV.

EXAMPLE X

A. Preparation of activated L-thyroxine

A solution of L-thyroxine, sodium salt hexahydrate (196.4 mg/0.221 mmol) in 2 ml DMSO was treated with PMBI (47.3 mg/0.221 mmol) in one portion at room temperature. The resultant yellow solution was stirred under argon at room temperature, protected from light, for an overnight period. The solution was then poured into excess ether to form a yellow oil which was allowed to settle followed by decanting the ether. After stirring for 10 minutes with fresh ether, the ether was again decanted and the oil dissolved in 20 ml of absolute methanol. Dropwise addition of 1N HCl gave a precipitate which was suction filtered, washed with excess 1N HCl and vacuum dried. Trituration with methylene chloride gave 210 mg (96% yield) of an N-maleiimide activated L-thyroxine as a pale yellow powder.

B. Linking of maleiimide activated L-thyroxine to thiolated alkaline phosphatase The derivatized L-thyroxine was reacted with alkaline phosphatase in accordance with the reaction scheme described in Example IV.

EXAMPLE XI

A. Preparation of activated digoxigenin

A solution of digoxigenin (53 mg/0.136 mmol) in 1 ml DMSO was treated with PMBI (29 mg/0.136 mmol) and the resultant yellow solution was stirred at room temperature under argon while protected from light for four hours. Dropwise addition of water (6 ml) gave a precipitate which was suction filtered, washed with excess water and vacuum dried. The crude residue was chromatographed on silica with 3% methanol in methylene chloride as the eluent. The 3 $\beta$-maleiimide activated digoxigenin product eluted as a pale yellow band after two impurity bands.

B. Linking of the maleiimide activated digoxigenin to thiolated alkaline phosphatase The derivatized digoxigenin was reacted with alkaline phosphatase according to the reaction scheme described in Example IV.

C. Preparation of a standard curve for a digoxin assay

The digoxigenin-alkaline phosphatase conjugate was used in a competitive digoxin assay carried out with standard solutions having known digoxin concentrations. The assays were carried out with assay modules of the type described in Example VII. A mouse anti-digoxin monoclonal antibody immobilized on the fibrous solid carrier was employed as the capture material. The assay method used was the same as that described in Example VIII. A standard curve having a desirably steep slope in the therapeutic concentration range was obtained.

EXAMPLE XII

A. Preparation of a hydroxyl-containing folic acid derivative

A solution of N-t-BOC-L-glutamic acid $\alpha$-benzyl ester (0.51 gm/1.50 mmol) and triethylamine (0.23 ml/1.65 mmol) in DMF (5 ml) was cooled under argon to $-40°$ C. and then treated in one portion with diphenyl phosphoryl azide (0.36 ml/1.65 mmol). The bath was allowed to warm slowly to $-5°$ C. over 20 minutes. After recooling to $-40°$ C., 3-amino-1-propanol (0.13 ml/1.65 mmol) was added in one portion and the bath allowed to slowly warn to room temperature overnight. The volatiles were removed under vacuum and the crude residue chromatographed on silica using 10% methanol in methylene chloride as eluent. The product eluted just after a trace of starting glutamic acid and upon evaporation of the appropriate fractions afforded the hydroxypropyl amide of N-t-BOC-L-glutamic acid, $\alpha$-benzyl ester as a clear syrup (0.5 gm/85% yield).

The hydroxypropyl amide obtained above (0.44 gm/1.13 mmol) was dissolved in ice cold methylene chloride (5 ml) and treated with anisole (0.12 ml/1.13 mmol) and trifluoroacetic acid (0.57 ml/7.4 mmol). The bath was allowed to slowly warm to room temperature and stirred for 4 hours. The volatiles were removed under vacuum and the residue chromatographed on silica using methanol-conc. ammonium hydroxide-methylene chloride (10:1:89) as eluent. The product eluted as the major band and upon evaporation of the appropriate fractions afforded the trifluoroacetic acid salt of the L-glutamic acid derivative (0.217 gm/65% yield) as a colorless oil (crystallized in the freezer).

A suspension of $N^{10}$-(trifluoroacetyl)pteroic acid (44 mg/0.10 mmol) in DMF (1 ml) was cooled under argon to $-10°$ C. To this was added triethyl amine (0.016 ml/0.112 mmol) and the trifluoroacetic acid salt obtained above (30 mg/0.10 mmol). After 5 minutes the mixture was further cooled to $-35°$ C. and diphenylphosphoryl azide (0.024 ml/0.112 mmol) was added in one portion. The bath was allowed to slowly warm to room temperature and stirred overnight. The volatiles were removed under vacuum to afford an amber oil which was triturated with excess acetonitrile for 5-10 minutes, suction filtered, washed and dried to afford a tan powder: 59 mg (85% yield). This material was used without further purification.

The previous product (54 mg/0.080 mmol) was suspended in 4 ml of a 50/50 ethanol/water solution and purged under argon for several minutes. To this stirred mixture at room temperature, under argon, was added 1N NaOH (0.24 ml/0.24 mmol) and the resulting yellow solution stirred, protected from the light for 3 hours. This solution was treated dropwise with 0.1N HCl (2.4 ml) to afford a yellow gelatinous material which was isolated by centrifugation. After one water wash/centrifugation cycle the residue was taken up in methanol and evaporated to dryness. The crude residue was dissolved in about 1 ml of isopropanol-conc. ammonium hydroxide-water (7:1:2) and chromatographed on silica with methylene chloride-methanol-conc. ammonium hydroxide (65:35:10) as eluent. The product eluted as a yellow band following a trace impurity band. The fractions containing the product were pooled and evaporated under vacuum to afford a yellow residue. The residue was dissolved in 4 ml 1N HCL and evaporated to dryness to afford 34 mg of the hydrochloric acid salt as a tan solid.

B. Activation of a hydroxyl-containing folic acid derivative.

The hydrochloric acid salt (34 mg; may contain several moles of water) was dissolved in DMSO (2 ml) and treated over a period of several days at room temperature with PMBI (approximately 20 equivalents) until thin layer chromatography revealed little or no remaining unreacted starting material [silica TLC with n-butanol:ethyl acetate:acetic acid:water (1:1:1:1) as eluent]. The product was isolated from the mixture by repeated treatments with ether and extraction of undesired organic material to give a yellow gummy residue. The residue was triturated with methylene chloride and then with hot acetonitrile (several cycles).

C. Linking of the activated folic acid to thiolated alkaline phosphatase

The folic acid derivative obtained above (72 $\mu$l of a 1 mg/ml solution in DMF) was added to 1.0 ml of 0.5 mg/ml thiolated alkaline phosphatase in pH3 TMSZ. After storage overnight in the refrigerator the conjugate was desalted on a PD-10 column. The protein fraction obtained contained the desired conjugate. UV absorption at $\lambda_{max} = 355$ nm confirmed the incorporation of folic acid in an approximate ratio of 3:1.

Although the invention has been described with respect to various preferred embodiments it is not intended to be limited thereto but rather those skilled in the art will recognize that variations and modifications maybe made therein which are within the spirit of the invention and the scope of the appended claims. For example, the rings of the aromatic and saturated carbocyclic moieties can be appropriately substituted further such as with the substituents disclosed. Thus, analogs possessing the advantageous features of the crosslinking compounds and conjugates of the present invention will be considered as equivalents thereof for the purposes of the claims herein.

What is claimed is:

1. A conjugate represented by the formula

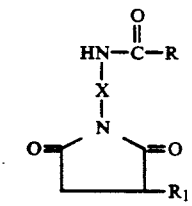

wherein X is alkylene, an aromatic carbocyclic moiety or a saturated carbocyclic moiety.
—R is the residue of an antigen having an alcohol and/or an amine group, where R is linked to the carbonyl group through an oxygen atom or a nitrogen atom; and
—$R_1$ is the residue of a protein having a thiol group, where $R_1$ is linked to the maleiimide moiety through a sulfur atom.

2. The conjugate as defined in claim 1 wherein —$R_1$ is the residue of an enzyme.

3. The conjugate as defined in claim 1 wherein X is alkylene having from 1 to 6 carbon atoms.

4. The conjugate as defined in claim 1 wherein —$R_1$ is the residue of an antibody.

5. The conjugate as defined in claim 1 wherein —R is the residue of a polypeptide.

6. The conjugate as defined in claim 1 wherein —R is the residue of a hormone.

7. The conjugate as defined in claim 1 wherein —R is the residue of a steroid.

8. The conjugate as defined in claim 1 wherein —R is the residue of vitamin $B_{12}$.

9. The conjugate as defined in claim 1 wherein —R is the residue of folic acid.

10. The conjugate as defined in claim 1 wherein —R is the residue of digoxigenin.

11. A conjugate represented by the formula

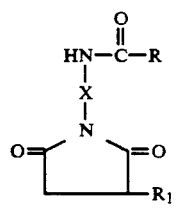

where X is phenyl, naphthyl or phenyl or naphthyl substituted with one or two alkylene groups having from 1 to 6 carbon atoms, attachment to the —NH moiety and/or the maleiimide moiety being effected through one of said alkylene groups;
—R is the residue of an antigen having an alcohol and/or an amine group, where R is linked to the carbonyl group through an oxygen atom or a nitrogen atom; and —$R_1$ is the residue of a protein having a thiol group, where $R_1$ is linked to the maleiimide moiety through a sulfur atom.

12. A conjugate represented by the formula

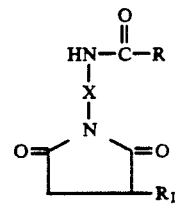

wherein X is a saturated carbocyclic moiety substituted with one or two alkylene groups having from 1 to 6 carbon atoms, attachment to the —NH moiety and/or the maleiimide moiety being effected through one of said alkylene groups;
—R is the residue of an antigen having an alcohol and/or an amine group, where R is linked to the carbonyl group through an oxygen atom or a nitrogen atom; and
—$R_1$ is the residue of a protein having a thiol group, where $R_1$ is linked to the maleiimide moiety through a sulfur atom.

13. A solid support for use in immunoassays comprising a conjugate represented by the formula

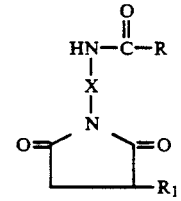

where X is alkylene, an aromatic carbocyclic moiety or a saturated carbocyclic moiety;
—R is the residue of a protein having an alcohol and/or an amine group, where R is linked to the carbonyl group through an oxygen atom or a nitrogen atom; and
$R_1$ is the residue of a solid support material having a thiol group, where $R_1$ is linked to the maleiimide moiety through a sulfur atom.

14. A solid support for use in immunoassays comprising a conjugate represented by the formula

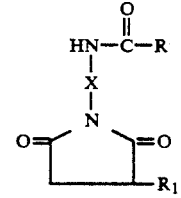

wherein X is alkylene, an aromatic carbocyclic moiety or a saturated carbocyclic moiety;
—R is the residue of a solid support material having an alcohol and/or an amine group, where R is linked to the carbonyl group through an oxygen atom or a nitrogen atom; and
$R_1$ is the residue of a protein having a thiol group, where $R_1$ is linked to the maleiimide moiety through a sulfur atom.

* * * * *